(12) United States Patent
Gimbel

(10) Patent No.: US 10,506,949 B2
(45) Date of Patent: Dec. 17, 2019

(54) DEVICE FOR DETERMINING THE LEVEL OF ILLICIT SUBSTANCES IN THE BREATH OF A PERSON

(71) Applicant: Dräger Safety AG & Co. KGaA, Lübeck (DE)

(72) Inventor: Doreen Gimbel, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 528 days.

(21) Appl. No.: 15/177,696

(22) Filed: Jun. 9, 2016

(65) Prior Publication Data

US 2016/0360995 A1 Dec. 15, 2016

(30) Foreign Application Priority Data

Jun. 12, 2015 (DE) .................. 10 2015 007 344

(51) Int. Cl.

| *A61B 5/08* | (2006.01) |
|---|---|
| *A61B 5/00* | (2006.01) |
| *A61B 5/02* | (2006.01) |
| *A61B 5/1172* | (2016.01) |
| *A61B 5/1171* | (2016.01) |
| *G06K 9/00* | (2006.01) |

(52) U.S. Cl.
CPC ............ *A61B 5/082* (2013.01); *A61B 5/0004* (2013.01); *A61B 5/0077* (2013.01); *A61B 5/02007* (2013.01); *A61B 5/1172* (2013.01); *A61B 5/1176* (2013.01); *A61B 5/4845* (2013.01); *A61B 5/742* (2013.01); *A61B 5/7405* (2013.01); *G06K 9/00255* (2013.01); *A61B 5/0064* (2013.01); *A61B 5/0075* (2013.01); *A61B 2503/22* (2013.01); *G06K 2009/00932* (2013.01); *G06K 2009/00939* (2013.01)

(58) Field of Classification Search
USPC .............................................. 600/473; 436/56
See application file for complete search history.

(56) References Cited

U.S. PATENT DOCUMENTS

| 4,843,377 A | 6/1989 | Fuller et al. | |
|---|---|---|---|
| 2005/0233459 A1* | 10/2005 | Melker | A61B 5/082 436/56 |

(Continued)

FOREIGN PATENT DOCUMENTS

DE 38 83 763 T2 3/1994

*Primary Examiner* — Nicole F Lavert
(74) *Attorney, Agent, or Firm* — McGlew and Tuttle, P.C.

(57) ABSTRACT

A device determines drug/alcohol content level in the breath of a person (1) with a stationary monitoring device (2), a communication unit (5) for data transmission to a central computer unit (4) and a hand-held device (3), connected via a data interface (6). The hand-held device has a mouthpiece (7) to receive a breath sample in a sample-receiving unit (18). An analysis unit (8) determines and transmits a drug/alcohol level via the data interface (6) to the monitoring device (2). A camera unit (16) records a skin area (13) of the person (1). An identification unit (9) makes a comparison of a recognized pattern on the skin with a pattern stored in a memory and a control signal is generated in case a pattern deviation. A control (10) is configured to transmit image data and/or a violation of the rules for performing the test if a limit value is exceeded.

21 Claims, 3 Drawing Sheets

(56) References Cited

U.S. PATENT DOCUMENTS

| | | | |
|---|---|---|---|
| 2011/0053173 A1* | 3/2011 | Hood | G07F 17/32 |
| | | | 435/7.1 |
| 2013/0006068 A1 | 1/2013 | Gemer et al. | |
| 2014/0278229 A1* | 9/2014 | Hong | A63B 71/06 |
| | | | 702/160 |
| 2014/0358023 A1* | 12/2014 | Davis | G01N 33/497 |
| | | | 600/543 |

* cited by examiner

DEVICE FOR DETERMINING THE LEVEL OF ILLICIT SUBSTANCES IN THE BREATH OF A PERSON

CROSS REFERENCE TO RELATED APPLICATIONS

This application claims the benefit of priority under 35 U.S.C. § 119 of German Patent Application 10 2015 007 344.3 filed Jun. 12, 2015, the entire contents of which are incorporated herein by reference.

FIELD OF THE INVENTION

The present invention pertains to a device for determining the content of illicit substances in the breath, especially the breath alcohol content, of a person, with a stationary monitoring device, which has at least one communication unit for transmitting data to a central computer unit. A hand-held device, which can be connected at least temporarily to the monitoring device via a data trunk, is provided for giving the sample. The hand-held device has a mouthpiece, via which a breath sample of the person can be taken and, and an analysis unit, by which the drug level in the breath sample can be determined and information can be transmitted to the monitoring device on the fact that a limit value has been exceeded at least when a limit value is exceeded. Furthermore, the monitoring device has a control, which is configured such that the exceeding of a limit value and a violation of rules for performing the test can be transmitted to the central computer unit.

BACKGROUND OF THE INVENTION

Various technical solutions are known in the field of monitoring persons with respect to the use of illicit substances, especially alcohol or other drugs. The testing of a breath sample is performed with prior-art systems optionally either at different sites by means of a mobile breath alcohol measuring device, for example, for monitoring vehicle drivers, or at fixed locations, especially for monitoring persons subject to house arrest rules.

Mobile devices are often used by the police or other regulatory agencies, which exercise official duties, in order to test especially vehicle drivers for the use of illicit substances. Stationary devices are installed, by contrast, above all in the household of a person who has been sentenced to house arrest in order to monitor compliance there with the house arrest rules, especially with respect to the ban on the use of illicit substances.

It may thus be necessary for various reasons to compare the identity of a person giving a sample with the person to be monitored. This is especially true in case of persons who have become noticed on several occasions because of alcohol-related offenses and must therefore use a monitoring system for monitoring the alcohol level at home.

At the beginning of such a measure, the person to be monitored must give a biometric sample as a basis for verification. This is preferably a fingerprint or a photo. In the further course of the measure, the person to be monitored must give a sample at fixed intervals in order to have, for example, the alcohol level in the breath checked. The agreement of the identity of the person giving the sample with the person to be monitored based on the biometric sample should be checked without the person giving the sample having to be excessively cooperative. It is essential for this that the handling of the corresponding monitoring systems is simple and does not call for any special requirements adapted to the conditions prevailing in the area surrounding the monitoring system, especially on light and noise conditions. A special biometric characteristic of the person to be monitored is recorded in the prior-art systems that check the identity of a person who must give a breath sample, usually before the beginning of the test proper, and compared with a biometric reference characteristic stored in the system. Fingerprints or photos of the person to be monitored are usually recorded/taken and analyzed as a basis of verification in prior-art systems.

A house arrest system, which is a detention and person monitoring system for prisoners or for persons conditionally released from custody on probation, who are subject to house arrest, house detention or a so-called unsupervised custody, is known in this connection from DE 38 83 763 T2. It is possible by means of the system described to monitor the presence of the prisoner at an unsupervised location and at the same time to monitor compliance with certain custody rules. A stationary device, which is optionally equipped with different means for detecting and monitoring biometric characteristics of the person to be monitored, is provided for this. In addition to the determination of the breath alcohol content of the person to be monitored, it is possible with the technical solution described to detect at least one biometric characteristic, e.g., a visible image information, a voice print or a fingerprint, in order to compare this detected characteristic with a known characteristic stored in the system. In case of violation of the custody rules or of the rules for properly performing the test, an external agency is informed of this by means of a suitable electronic message.

SUMMARY OF THE INVENTION

Based on the prior-art monitoring system as well as the above-described problem, a basic object of the present invention is to perfect a device for determining the drug level in the breath, especially the breath alcohol content, of a person being monitored such that an accurate identification of the person can be performed with simple means and above all largely without time delay in the test procedure. Furthermore, the device to be provided or the method used shall make it possible to accurately check the identity of the person to be monitored even under different ambient conditions, especially varying light conditions. It should be borne in mind in this connection that the persons to be monitored are often uncooperative and attempt to take advantage of weak points or possible malfunctions of the monitoring system. The monitoring system should thus be able to guarantee both an unambiguous identification of the person to be monitored and the provision of accurate test results for the breath alcohol content of the person to be monitored and to transmit them to an external agency, for example, a probation officer. Based on the special intended use, it should, furthermore, be borne mind that the hardware and the software that are used must be made comparatively robust.

In the prior-art systems, the identification of the person to be monitored is often not performed immediately with the device intended for sampling, but only after the data have been transmitted to a server. This generates large quantities of data to be transmitted, so that another object of the present invention is to provide a monitoring system in which only the data that are absolutely most necessary are transmitted.

According to the present invention a device for determining the drug level, especially the alcohol content, in the breath of a person is provided comprising a stationary monitoring device, which has at least one communication unit for transmitting data to a central computer unit, and with a hand-held device, which can be connected to the monitoring device via a data interface at least temporarily. Data can be exchanged via this interface between the mobile hand-held device and the stationary monitoring device either unidirectionally or bidirectionally as needed. The hand-held device has, further, a mouthpiece, by means of which a breath sample of the person being monitored can be taken, an analysis unit, by which the drug level in the breath sample can be determined and can be transmitted to the monitoring device via the data interface, at least in the case in which a limit value is exceeded, as well as at least one identification unit, with which a variance comparison of at least one biometric characteristic of the person can be performed during and/or after the breath sample has been given to identify the person intended for giving the breath sample. The monitoring device has, furthermore, a control, which is configured such that the fact that a limit value was exceeded and/or rules on performing the test have been violated can be transmitted to the central computer unit. A skin area of the person can be recorded with the identification unit by means of a skin area recording device that is an image recording unit in the form of a camera and/or scanner unit and a comparison of at least one recognized pattern of a structure located on the skin, in the skin and/or in the subcutaneous tissue with a pattern stored in a memory can be performed. A control signal is generated by a control of the hand-held device for initiating at least one measure in case of a detected deviation between the recognized pattern and the stored pattern.

It is essential for the technical solution according to the present invention that the hand-held device, which can be connected to the stationary monitoring device via the data interface at least temporarily, has a computer unit or processor of its own for verifying the user during the giving of the sample. The data needed for the verification of the person, especially the pattern of a structure on, in and/or under the skin are stored in the hand-held device. The identity of the person giving the sample is verified during the performance of the test with the giving of a sample, each time a sample is given. It is ensured in this manner that a data exchange between the hand-held device and the stationary monitoring device is limited to the necessary minimum. Data are preferably transmitted only in case a limit value is exceeded or in case of an unauthorized deviation from the rules for performing the test, especially if it cannot be ruled out that the breath sample was given by a person other than the person intended to give the sample.

According to a special embodiment of the present invention, the camera unit and/or scanner unit for recording a skin area of the person giving the sample is integrated in the hand-held device such that a skin area of the person's face can be recorded at least while the person is holding the mouthpiece in his mouth. The camera unit and/or scanner unit is advantageously arranged in the hand-held device such that a skin area, which is located laterally from the nose, is recorded. The recorded data, especially a pattern of a special structure in, on or under the skin, are compared with data stored in the system. The arrangement of veins or arteries in the skin area being recorded is preferably used to verify the person giving the sample.

According to an alternative embodiment of the present invention, the camera unit and/or scanner unit is integrated in the hand-held device such that a skin area of a hand or of an arm of the person can be recorded while the breath sample is being given. The camera unit preferably has a suitable lens in this case so that a skin area located at a comparatively great distance from the camera unit and/or scanner unit can be reliably recorded. Regardless of whether a skin area located on the face or a skin area of an arm or of a hand is used to verify the person giving the sample, it may be preferable to use a structure of veins and/or arteries in this area as a pattern to be analyzed.

In a special embodiment, the camera unit and/or scanner unit records images in the infrared range. Thus, it is an IR camera or an IR scanner in this case. Special capillaries in the face of the person giving the sample are preferably recorded with the image recording unit integrated in the hand-held device. Based on the correct connection of the hand-held device during the giving of the sample, it is guaranteed that the same area of the user's face is always scanned by the image recording unit, especially an IR camera, in the hand-held device, without additional cooperation being necessary on the part of the user. The conditions at the location at which the sample is given, above all the light conditions, also do not play any role for the recording of the pattern, which will be used as the basis for a later comparison.

In a special variant of the present invention the identification unit has at least one device for detecting a fingerprint and/or a camera for taking a photo of the face of the person in addition to the camera unit and/or scanner unit, with which a skin area of the person giving the sample is recorded. An additional verification of the person giving the sample can preferably be achieved by providing a fingerprint scanner at the hand-held device and the safety of the system against manipulations can be increased. Based on the taking of a photo of the person giving the sample, it is, furthermore, possible to record an image of the person giving a sample at certain times before, during or after the sample has been given and to transmit this, if needed, to an external agency via the stationary monitoring device.

The control of the hand-held device is configured in a special embodiment such that in case a deviation is detected between the recognized pattern and the stored pattern, this deviation is classified as a violation of the rules for performing the test and is transmitted to the monitoring device via the data interface. It may be preferable in this connection that information in respect to the violation of the rules for performing the test, the fact that a limit value was exceeded and/or the violation of a measured value is transmitted to the monitoring device via the data interface only in case of a detected deviation from the rules for performing the test and/or in case a limit value is exceeded. It is advantageous in connection with the system described to minimize the data volume, which must be exchanged between the individual components, namely, the hand-held device, the stationary monitoring device as well as the external computer unit, to a minimum. A corresponding logic is advantageously provided for this in the corresponding devices, especially the mobile hand-held device as well as the stationary monitoring device, so that only violations of the testing rules and/or cases in which limit values are exceeded, especially of the permissible drug or breath alcohol level in the breath, are transmitted. As long as the verification of the person giving the sample, the monitoring of the individual steps during the test performance as well as the drug level in the breath of the person giving the sample fail to show deviations from the permissible values, data transmission is not preferably performed and the person giving the sample is advantageously only informed that the recorded values are in order.

The described device for monitoring the drug level, especially the alcohol level in the breath of a person giving a sample, which offers at the same time the possibility of verifying the identity of the person giving the sample, is preferably used to test a drug concentration in the breath of a machine operator, a road user and/or a person who is living subject to terms of detention and/or probation. Furthermore, it is conceivable to use the device according to the present invention in connection with the performance of access control to rooms, vehicles or machines. It is thus possible by means of the device according to the present invention to ensure that persons under the influence of drugs or alcohol do not perform certain activities or are not granted access to rooms in which safety-relevant devices are set up or special jobs must be performed.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a schematic view of a hand-held device with integrated camera unit for recording a skin area of the person giving the sample as well as with a communication unit, by means of which the hand-held device can exchange data with a stationary monitoring device via a data interface, as well as.

DESCRIPTION OF THE PREFERRED EMBODIMENTS

Figure 1:
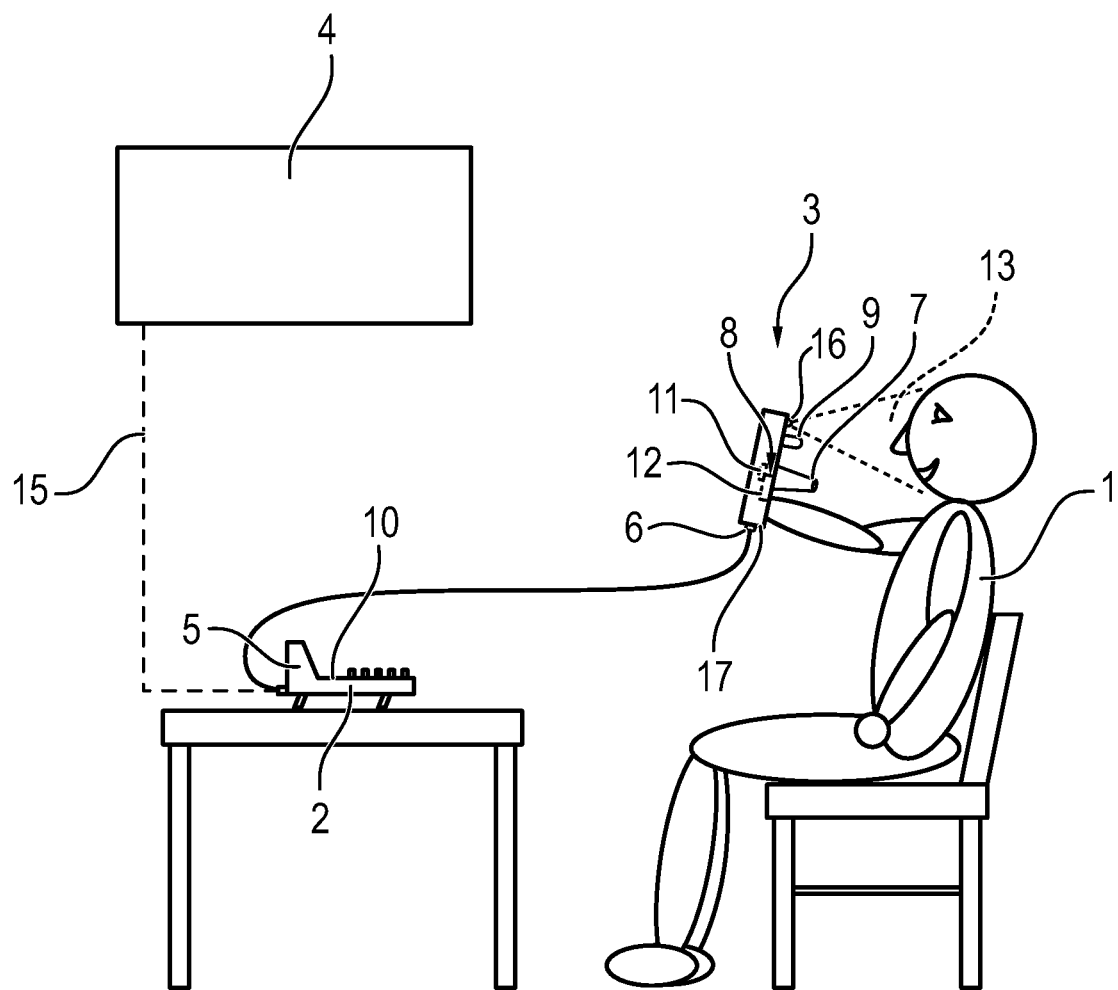
FIG. 1 is a schematic view of a device for detecting the breath alcohol content of a person as well as for identifying the person giving the sample.

Referring to the drawings, FIG. 1 shows a system for testing the breath alcohol content of a person 1. The system has a stationary monitoring device 2, which communicates with an external computer 4, which is located, for example, at a regulatory agency, by means of a communication unit 5. Furthermore, a hand-held device 3 is provided, which can be connected to the stationary monitoring device 2 at least temporarily via a data interface 6, and which can exchange data with this as needed unidirectionally or bidirectionally.

The concept of unsupervised custody as a means of probation and as an alternative to confinement in a penal institution has been known for a long time. The persons who are subject to house arrest are often subject to additional requirements, which pertain especially to the consumption of drugs, especially alcohol. An essential feature of devices for monitoring compliance with the rules governing house arrest is thus that they are also regularly used to monitor the level of drugs, especially the alcohol content in the breath of the person to be monitored. At the same time, it should be borne in mind this connection that a breath sample should also be given by the correct person, so that corresponding devices are obligatory for verifying the identity of the person giving the sample. In addition to corresponding systems, which are used within the framework of the monitoring of house arrest rules, corresponding systems are, furthermore, generally known, with which, for example, persons who had already often operated a vehicle under the influence of alcohol also must be monitored at home, especially before they go for a drive by car.

The device according to FIG. 1 is suitable for monitoring a person 1, who is under house arrest or is subject to the regulations concerning alcohol consumption.

The person 1 to be monitored must give a breath sample at certain intervals or upon request. The corresponding breath sample is given via a mouthpiece 7 into a sample-receiving unit 18 of the hand-held device 3, in which the breath sample is analyzed by means of an analysis unit 8 and the breath alcohol content is determined. If the breath alcohol content detected exceeds a permissible limit value, a corresponding report, which contains an indication of the violation and at the same time the determined breath alcohol content, is generated and sent to the stationary monitoring device 2 via the data interface 6. As soon as the stationary monitoring unit 2 has received a corresponding message, it establishes a data link 15 with an external computer unit 4, which is located, for example, in the office of a probation officer or in a regulatory agency in charge of the monitoring of the person 1. Finally, a message on the limit value violation as well as the breath alcohol value is finally transmitted via this data trunk 15 to the external computer 4.

The identity of the person 1 is first checked before the person 1 being monitored gives the breath sample via the mouthpiece 7 into the sample-receiving unit 18 in the interior of the hand-held device 3. Biometric characteristics of the person 1 to be monitored are stored for this in a memory 11, the structure of the veins in the area of the face in a skin area 13 next to the nose being stored as a pattern to be monitored in the exemplary embodiment being shown. The hand-held device 3 has, furthermore, an identification unit 9 with a camera unit 16, which scans an area in the face of the person being monitored next to the nose, the recording field being markedly larger than the area ultimately used for checking the identification. The verification of the identity of the user 1 by the vein scan has a high recognition rate. Since the vein scan is performed by means of a camera unit 16 in the form of an IR (infrared) scanner, the recording is nearly independent from the light conditions at the sampling site.

According to the exemplary embodiment explained in connection with FIG. 1, the vein scan is performed in a skin area 13 on the face of the person 1 being monitored. As an alternative, for example, one may scan a skin area 13 in the area of the hand of the person 1 giving the sample. To make, moreover, the identification of the person giving the sample 1 even more reliable, the hand-held device 3 shown in FIG. 1 contains, in addition to the camera unit 16 for the IR scan of a skin area 13, another camera 17 for the graphic recording of the face of the person giving the sample. A conventional photo is thus taken with this additional camera 17, preferably in digital form.

In addition to the comparison of the recorded vein structure with a desired structure being stored in the memory 11, the recorded image, i.e., the photo, is stored for documentation purposes in a memory of the hand-held device 3 and is assigned in this case to the particular instance in which the sample is given. If the analysis unit 8 detects a deviation, especially of the detected vein structure from the stored structure, the person giving the sample 1 at first receives an indication via the display 14 of the hand-held device 3 that the test was invalid and shall be repeated by the person giving the sample. If another invalid test is performed, either because the recorded vein structure differs from the stored structure or because the detected breath alcohol content exceeds a permissible limit value, a corresponding error message is transmitted via the data interface 6 to the stationary monitoring device 2. The stationary monitoring device 2 will then again establish a data link 15 with the external computer unit 4 and transmits the error message together with the stored photo for documentation as soon as the data link 15 has been established.

It is essential in the device according to the present invention that data are transmitted only if a violation of the testing rules and/or a breath alcohol value exceeding the permissible breath alcohol level has been detected. The data sets to be transmitted are limited to the absolutely necessary extent in this way.

Figure 2:
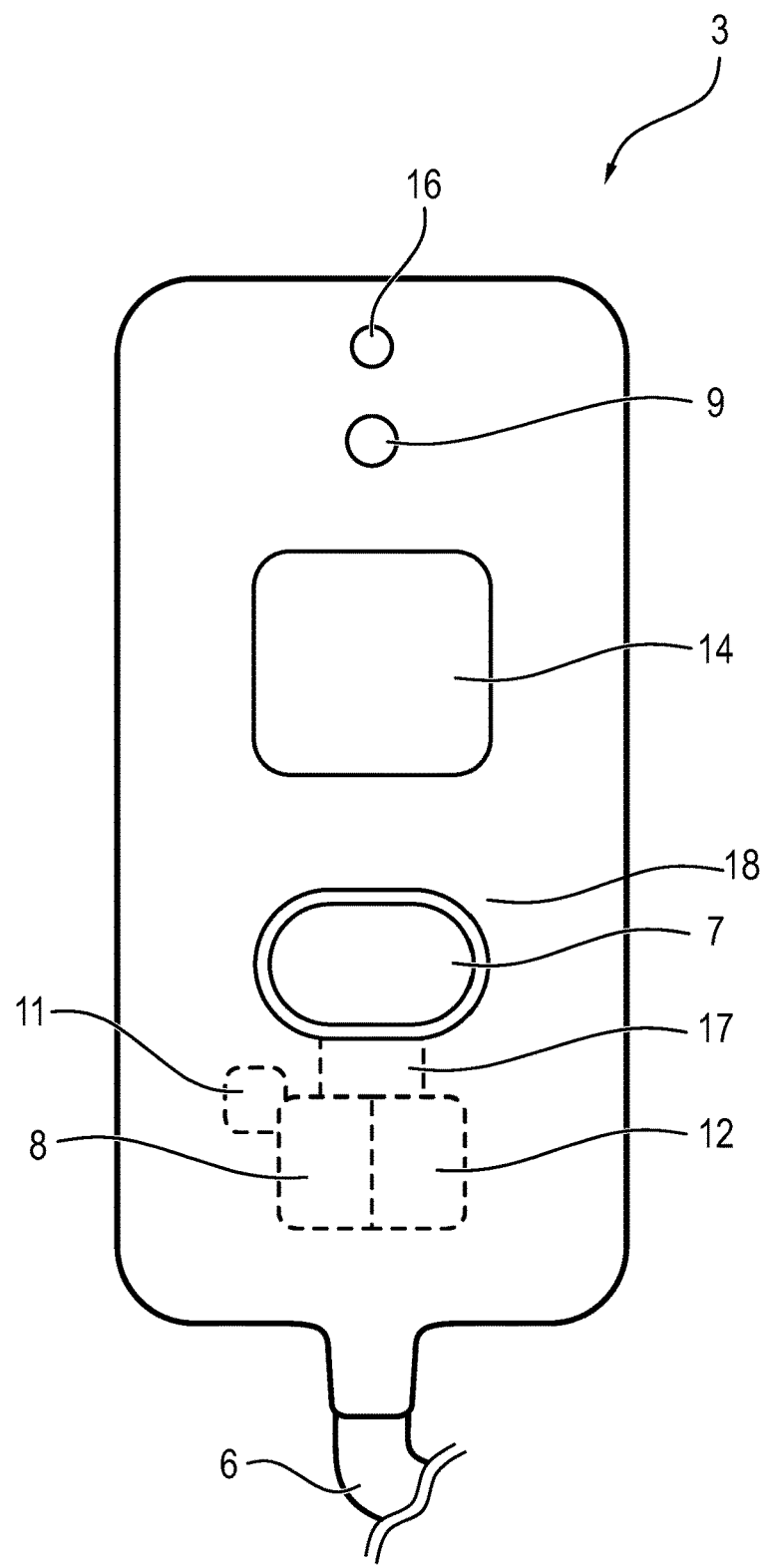

FIG. 2 shows a hand-held device 3, which is provided as part of a device configured according to the present invention for monitoring the breath alcohol content of a person 1 to be monitored as well as for reliably identifying this person 1 by means of an identification unit 9. The hand-held device 3 may optionally be connected with the stationary monitoring device 2 via a wired or wireless interface 6. To enable the person 1 to be monitored to give a breath sample, a mouthpiece 7 is provided, through which the breath sample can be given, and it enters a sample-receiving unit 18. The mouthpiece 7 preferably has a disposable element, which the person 1 being monitored can dispose of each time after having given a breath sample. As an alternative, the mouthpiece 7 is configured such that it is removable and can be cleaned in an especially simple manner.

Furthermore, the hand-held device 3 has an analysis unit 8, with which the breath alcohol content is determined and compared with a stored, permissible limit value. If the detected breath alcohol content is below the permissible limit value, only the message that a test was successfully performed is outputted to the person 1 giving the sample via the display 14 after it was verified by the identification unit 9 that the person is also the person 1 intended to give the sample. If, by contrast, the breath alcohol content exceeds the permissible limit value, the information on the fact that the limit value was exceeded and the determined breath alcohol value are transmitted via the data interface 6 to the stationary monitoring device 2. As an alternative, the giving of another breath sample is first requested in this case and a corresponding message is transmitted to the stationary monitoring device 2 only as soon as this likewise shows that the limit value was exceeded.

Moreover, the identification unit 9 of the hand-held device 3 has a camera unit 16, with which a skin area 13 of the person 1 giving the sample can be scanned. The structure of the veins and arteries located within the skin as well as in the subcutaneous tissue is recorded here by means of reflected infrared rays, and this structure is compared with a previously recorded structure, which is likewise stored in a memory 11 of the hand-held device 3. If the detected vein structure and the structure stored in the hand-held device 3 agree within a tolerance range, it is determined that the breath sample was given by the correct person 1 and the giving of the breath sample is rated as being permissible. If it is determined, by contrast, that the recorded structure of veins, capillaries and/or arteries shows inadmissible deviations from the stored structure stored, an inadmissible test performance is detected by the analysis unit 8, and a signal is generated by the hand-held device control unit 12 on the basis of this violation, so that the person 1 giving the sample is again requested via the display 14 to give another breath sample. Such a violation of the rules for performing the test may be documented and/or reported to a monitoring agency via the monitoring device 2.

The capillary scan in the face represents the simplest, most reliable and most tamper-proof method for verifying the identity of the person 1 giving the sample. Thus, this method is characterized especially in that no combination with additional test methods, e.g., the taking of a photo or of a fingerprint, is absolutely necessary. The same section is always recorded on the face of the person 1 giving the sample by the preferably used IR camera and/or IR scanner unit in the hand-held device 3 and can be used for the verification of the person 1 giving the sample. It is ensured hereby that the person 1 giving the sample is, in reality, also identical to the person being monitored. The essential components of the hand-held device 3 are the sample-receiving unit 18 with the mouthpiece 7, the identification unit 9 with camera unit and/or scanner unit 16 for recording the skin area 13 of the person 1 giving the sample, an analysis unit 8 for determining the breath alcohol content and for comparing the recorded structure with a desired structure, as well as a communication unit 5 of the hand-held device 3 for establishing a data link with the stationary monitoring device 2, especially in order to transmit error messages. The overall system also comprises, furthermore, another unit for data communication, which makes data transmission possible from the stationary monitoring device 2 to an external computer unit 4.

Both the stationary monitoring device 2 and the hand-held device 3 are configured such that outside tampering with the devices 2, 3 are prevented or are at least documented in the device and possibly transmitted to the monitoring agency via a data link 15 between the stationary monitoring device 2 and the external computer unit 4.

Figure 3:
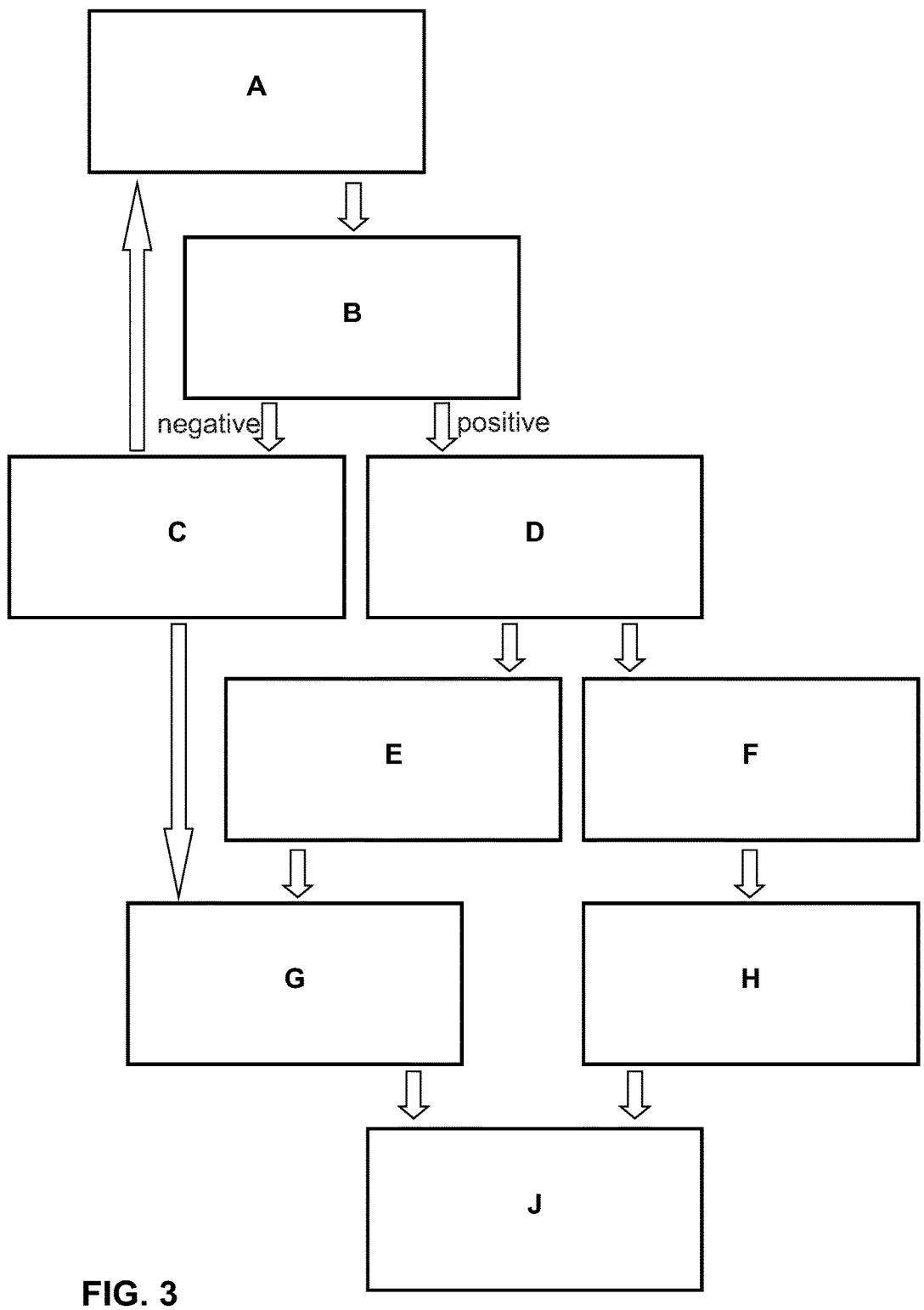
FIG. 3 is a flow chart of a method for monitoring the breath alcohol concentration of a person to be monitored.

FIG. 3 shows a flow chart, on the basis of which the course of testing the breath alcohol content of a person 1 giving a sample as well as of the identity of the person giving the sample and of the person being monitored will be explained. The establishment of the identity of the person giving the sample and of the person being monitored is defined in this case such that the person being monitored is the same person who has also given the sample. By contrast, it is, in principle, irrelevant in this step what person is involved.

A breath sample is first given in step "A" and a vein structure is recorded by means of an IR camera 16 in the facial area of the person giving the sample. As an option, a photo of the person 1 giving the sample may also be taken in this step with an additional camera 17.

A comparison of the vein structure recorded with a stored pattern as well as possibly a comparison between a photo taken and a stored photo are performed in step "B" by means of the analysis unit 8. If the recorded vein structure or the photo taken deviates from the stored image data, it is indicated to the person 1 giving the sample in a step "C" that the verification has led to a negative result and step "A" with the giving of a breath sample and at least one recording of a venous structure must be repeated. If the verification of the image data in step "B" leads, by contrast, to a positive result, the determination of the breath alcohol concentration begins in the analysis unit in a step "D."

Should it be determined in step "C" that the verification of the person giving the sample was repeatedly non-positive, especially twice, it is possible to make provisions in the system for this information to be transmitted to the stationary monitoring device together with the relevant image data according to step "G.". It is possible to store this error message with the corresponding image data in an event file in the memory and then transmit it again to an external computer in a repeated step "J.".

If the analysis performed leads to the result that the determined breath alcohol concentration is below a permissible limit value, this is signaled to the person who gave the sample with a display in a step "E" on the display unit. The result of this analysis may likewise be transmitted in a step "F" to the stationary monitoring device 2 and stored here in a step "H" in a memory in an event file. This event file may be transmitted to an external computer 4 in a step "J", and this transmission can be automated, especially event-controlled, or initiated by manual file retrieval.

If the analysis in step "D" leads to the result that the breath alcohol concentration determined exceeds a permissible limit value, this is displayed to the person 1 giving the sample on the display 14 in a step "E" and this event is stored in step "G," together with the recorded vein structure and possibly with the recorded image, to the stationary monitoring device 2, in which these data are stored, in turn, in an event file in the memory. This event file may, in turn, be transmitted in a step "J" to an external computer 4, and this transmission may be automated, especially in an event-controlled manner, or initiated by manual file retrieval.

It is thus essential in the technical solution according to the present invention that data are stored and transmitted to another device only as soon as an error is detected and the corresponding data are needed to document the error and for documentation.

While specific embodiments of the invention have been shown and described in detail to illustrate the application of the principles of the invention, it will be understood that the invention may be embodied otherwise without departing from such principles.

APPENDIX

List of Reference Numbers

1 Person
2 Stationary monitoring device
3 Hand-held device
4 External computer unit
5 Communication unit
6 Data interface of hand-held device/monitoring device
7 Mouthpiece
8 Analysis unit
9 Identification unit
10 Control of the monitoring device
11 Memory
12 Control of hand-held device
13 Skin area of the person
14 Display
15 Data link
16 Camera unit for recording a skin area
17 Camera unit for taking a photo
18 Sample-receiving unit

What is claimed is:

1. A device for determining a level of drug in the breath of a person, the device comprising:
   a stationary monitoring device with a communication unit configured to transmit data to a central computer;
   a data interface;
   a hand-held device connectable at least temporarily to the monitoring device via the data interface, the hand-held device comprising a mouthpiece for taking a breath sample of the person, an analysis unit configured to determine a level of drug in the breath sample and to transmit a determined drug level to the monitoring device via the data interface at least in a case of a drug limit value being exceeded and an identification unit configured for a variance comparison of at least one biometric characteristic of the person, performed before or during or after or any combination of before, during and after the breath sample was given for identifying the person intended to give the breath sample;
   a monitoring control unit connected to the monitoring device, the monitoring control unit being configured to transmit to the central computer upon the drug limit value being exceeded or upon a violation of rules for performing the test or upon both the drug limit value being exceeded and a violation of rules for performing the test, wherein the identification unit comprises:
   a memory with a stored pattern of a pattern structure located on the skin or in the skin or in the subcutaneous tissue or in any combination of on the skin, in the skin and in the subcutaneous tissue of the person; and
   a skin area recording device comprising a camera or scanner unit or both a camera and a scanner unit, the identification unit being configured to record a skin area of the person of at least one recognized pattern of a pattern structure located on the skin or in the skin or in the subcutaneous tissue or in any combination of on the skin, in the skin and in the subcutaneous tissue and to compare the at least one recognized pattern of the recorded skin area with the stored pattern, stored in the memory; and
   a hand-held device control connected to the hand-held device, wherein the hand-held device control is configured to generate a control signal for initiating at least one measure if a deviation is detected between the recognized pattern and the stored pattern.

2. A device in accordance with claim 1, wherein the skin area recording device is integrated in the hand-held device with the camera or scanner unit or camera and scanner unit disposed relative to the mouthpiece such that a skin area of the face of the person is recorded at least while the person is holding the mouthpiece in the person's mouth.

3. A device in accordance with claim 1, wherein the skin area recording device is integrated in the hand-held device with the camera or scanner unit or camera and scanner unit disposed relative to the mouthpiece and/or relative to a hand holding portion of the hand-held device such that a skin area of a hand or of an arm or of both a hand and an arm of the person is recorded while the breath sample is being given.

4. A device in accordance with claim 1, wherein the at least one recognized pattern is a structure of an arrangement of veins that is recorded by the identification unit and compared with a stored structure of an arrangement of veins.

5. A device in accordance with claim 1, wherein the skin area recording device is configured as an infrared camera or an infrared scanner or as both an infrared camera and an infrared scanner.

6. A device in accordance with claim 1, wherein the identification unit further comprises, in addition to the camera unit configured to record the skin area, at least one device for detecting a fingerprint or a camera for taking a photo of the face of the person or both at least one device for detecting a fingerprint and a camera for taking a photo of the face of the person.

7. A device in accordance with claim 1, further comprising an output device comprising a display unit or a loudspeaker or both a display unit and a loudspeaker, wherein the hand-held device control is further configured to generate a control signal for outputting a request to repeat the test via the output device to the person if a deviation is detected between the recognized pattern and the stored pattern.

8. A device in accordance with claim 1, wherein the hand-held device control is configured such that in case a deviation is detected between the recognized pattern and the stored pattern, this deviation is classified as a violation of the rules for performing the test and is transmitted to the monitoring device via the data interface.

9. A device in accordance with claim 1, wherein the hand-held device control is further configured such that information relating to a limit value being exceeded or a measured value is transmitted to the monitoring device via the data interface only upon detecting that a limit value was exceeded.

10. A method for determining a level of drug in the breath of a person, the method comprising the steps of:

providing a device comprising a stationary monitoring device with a communication unit configured to transmit data to a central computer, a data interface, a hand-held device connectable at least temporarily to the monitoring device via the data interface, the hand-held device comprising a mouthpiece for taking a breath sample of the person, an analysis unit configured to determine a level of drug in the breath sample and to transmit a determined drug level to the monitoring device via the data interface at least in a case of a drug limit value being exceeded and an identification unit configured for a variance comparison of at least one biometric characteristic of the person, performed before or during or after or any combination of before, during and after the breath sample was given for identifying the person intended to give the breath sample, a monitoring control unit connected to the monitoring device, the monitoring control unit being configured to transmit to the central computer upon the drug limit value being exceeded or upon a violation of rules for performing the test or upon both the drug limit value being exceeded and a violation of rules for performing the test, wherein the identification unit comprises a memory with a stored pattern of a pattern structure of physical features located on the skin or in the skin or in the subcutaneous tissue or in any combination of on the skin, in the skin and in the subcutaneous tissue of the person and a skin area recording device comprising a camera or scanner unit or both a camera and a scanner unit, the identification unit being configured to record a skin area of the person of at least one recognized pattern of a pattern structure of physical features located on the skin or in the skin or in the subcutaneous tissue or in any combination of on the skin, in the skin and in the subcutaneous tissue and to compare the at least one recognized pattern of the recorded skin area with the stored pattern, stored in the memory; and a hand-held device control connected to the hand-held device, wherein the hand-held device control is configured to generate a control signal for initiating at least one measure if a deviation is detected between the recognized pattern and the stored pattern; and testing a breath drug concentration of a person with the provided device.

11. A method according to claim 10, wherein the person tested is a machine operator, a road user or a person who is living subject to the requirements of detention or probation or both detention and probation.

12. A method according to claim 10, further comprising using the testing for access control to a room, space or vehicle.

13. A method in accordance with claim 10, wherein the skin area recording device is integrated in the hand-held device such that a skin area of the face of the person is recordable at least while the person is holding the mouthpiece in the person's mouth.

14. A method in accordance with claim 10, wherein the skin area recording device is integrated in the hand-held device such that a skin area of a hand or of an arm or of both a hand and an arm of the person is recordable while the breath sample is being given.

15. A method in accordance with claim 10, wherein the at least one recognized pattern is a structure of an arrangement of veins that is recorded by the identification unit and compared with a stored structure of an arrangement of veins.

16. A method in accordance with claim 10, wherein the skin area recording device is configured as an infrared camera or an infrared scanner or as both an infrared camera and an infrared scanner.

17. A method in accordance with claim 10, wherein the identification unit further comprises, in addition to the camera unit configured to record the skin area, at least one device for detecting a fingerprint or a camera for taking a photo of the face of the person or both at least one device for detecting a fingerprint and a camera for taking a photo of the face of the person.

18. A method in accordance with claim 10, further comprising an output device comprising a display unit or a loudspeaker or both a display unit and a loudspeaker, wherein the hand-held device control is further configured to generate a control signal for outputting a request to repeat the test via the output device to the person if a deviation is detected between the recognized pattern and the stored pattern.

19. A method in accordance with claim 10, wherein the hand-held device control is configured such that in case a deviation is detected between the recognized pattern and the stored pattern, this deviation is classified as a violation of the rules for performing the test and is transmitted to the monitoring device via the data interface.

20. A method in accordance with claim 10, wherein the hand-held device control is further configured such that information relating to a limit value being exceeded or a measured value is transmitted to the monitoring device via the data interface only upon detecting that a limit value was exceeded.

21. A method in accordance with claim 10, wherein the step of testing a breath drug concentration of a person with the provided device step comprises testing a breath alcohol concentration of the person with the provided device.

* * * * *